United States Patent [19]
Sarkar

[11] 3,963,484
[45] June 15, 1976

[54] DENTAL AMALGAM ALLOYS

[76] Inventor: Nikhil K. Sarkar, 1415 W. Lunt Ave., Apt. 503, Chicago, Ill. 60626

[22] Filed: Aug. 20, 1974

[21] Appl. No.: 498,930

[52] U.S. Cl. ............................... 75/173 C; 75/169
[51] Int. Cl.² ............................................. C22C 5/08
[58] Field of Search .................. 75/173 C, 169, .5 R

[56] References Cited
UNITED STATES PATENTS

| | | | |
|---|---|---|---|
| 1,963,085 | 6/1934 | Gray | 75/173 C |
| 2,281,991 | 5/1942 | Poetschke | 75/173 C |
| 3,305,356 | 2/1967 | Youdelis | 75/173 C X |
| 3,841,860 | 10/1974 | Wolf | 75/.5 R |

*Primary Examiner*—L. Dewayne Rutledge
*Assistant Examiner*—E. L. Weise

[57] ABSTRACT

A two-component amalgam alloy system comprises as a first component a standard silver-tin amalgam alloy, and as a second component a copper base alloy. The two components are intermixed and amalgamated with mercury to form a dental amalgam from which the highly corrodible tin-mercury (gamma-2) phase has been removed and the readily tarnishable and inter-granular fracturable (brittle) silver-mercury (gamma-1) phase can be reduced.

18 Claims, No Drawings

DENTAL AMALGAM ALLOYS

BACKGROUND OF THE INVENTION

Conventional dental amalgams are among the most widely used restorative materials employed in dentistry. These amalgams are made by mixing a dental amalgam alloy with mercury, the amount of mercury varying from 40% to 60% by weight of the alloy, to obtain the necessary and desirable working quality or plasticity required, in accordance with the manufacturer's recommendations.

The standard or conventional amalgam alloy composition as currently certified by the American Dental Association (ADA) comprises:

| | |
|---|---|
| Silver | 65.0% minimum |
| Tin | 29.0% maximum |
| Copper | 6.0% maximum |
| Zinc | 2.0% maximum |

An amalgam alloy of the above composition containing mercury up to 3.0% maximum in addition, is reportedly used extensively in European countries but is not very popular in the United States. Such alloys are described as "preamalgamated" alloys.

Metallurgically, the principal component of the standard or conventional amalgam alloy is the gamma phase, $Ag_3Sn$. The amalgamation reaction involves the solution of $Ag_3Sn$ in mercury (Hg), from which a precipitation of silver-mercury ($Ag_2Hg_3$, gamma-1 phase) and tin-mercury ($Sn_7Hg$, gamma-2 phase) takes place. The setting or hardening of the amalgam, which occurs in the tooth cavity, is associated with and responsive to these metallurgical changes.

The amount of tin-mercury (gamma-2) phase and the silver-mercury (gamma-1) phase increases with the amount of mercury added to the silver-tin (gamma) phase. In current clinical practice, wherein the mercury content ranges between 40–60% by weight of the amalgam alloy to which it is added, a major portion of the conventional alloy, in particulate form, will react with the mercury. Thus, in a hardened or set amalgam structure, one finds some unreacted silver-tin particles bonded or cemented together in a matrix of silver-mercury and tin-mercury compounds. Trace amounts of a copper-tin complex have also been detected in the microstructure of a set amalgam.

The tin-mercury (gamma-2) phase has been held responsible for the tarnish and corrosion failure of the conventional dental amalgam. It has been recognized that this is due to an electrochemical polarization, resulting in the deterioration of the tin-mercury (gamma-2) phase and an eventual weakening of the physical structure. It has also been found that the tarnish of such dental amalgams results from the attack on the silver-mercury (gamma-1) phase by sulfide ions generated from ingested food materials.

It has further been observed and recognized that both the tin-mercury (gamma-2) and the silver-mercury (gamma-1) phases are relatively weak, and the brittle failure of amalgam restorations is believed to occur through the initiation of cracks in the tin-mercury phase and the inter-granular fracture of the silver-mercury phase. Moreover, it has been found that the silver-mercury phase is responsible for the creep of dental amalgams which in turn is related to marginal fracture. These defects of conventional dental amalgams account for the principal limitations of amalgam restorations.

A relatively new amalgam alloy is one disclosed in Youdelis U.S. Pat. No. 3,305,356 issued Feb. 21, 1967 for "Dental Amalgam". An alloy marketed under this patent has attracted widespread attention in view of the reportedly improved clinical behavior of the amalgams. One of these alloys as marketed consists of a mechanical mixture of two silver-rich alloys or components. The first of these is a conventional amalgam alloy of the silver-tin (copper-zinc) type. The second component is a silver-copper (AgCu) eutectic alloy, combined with the conventional alloy in a ratio of two parts of the conventional alloy to one part of the eutectic, by weight. The amalgam made by these components, when combined with mercury in the 40–60% proportions, is reported to contain very little or no tin-mercury (gamma-2) phase, but the amount of silver-mercury phase produced is not any less than that which is observed in a conventional amalgam for equivalent mercury content. Other microstructural constituents believed to be present in this amalgam include copper-tin complex, and unreacted silver-tin (gamma) phase and silver-copper (AgCu) eutectic particles.

According to the Youdelis patent disclosure and as expected, any significant oxidation of the silver-copper eutectic tends to retard amalgamation and unduly increase the setting time of the amalgam. Further, it has been reported that if the copper concentration in the conventional dental alloy exceeds a maximum of 6.0%, as stated in the ADA specification, the resultant amalgam exhibits excessive expansion and a greater tendency to tarnish. These undesirable qualities or characteristics, based upon a copper content of greater than 6.0%, appear to be due, at least metallurgically, to the presence of $Ag_5Sn$ (beta phase) in the alloy microstructure. A correlation has been found to exist between the presence of such a beta phase and an uncontrollable (i.e., unrestricted) expansion of the amalgam. Further, the $Ag_3Sn$ (gamma) phase has a sulfide tarnish resistance greater than that found in silver-tin alloys containing higher amounts of silver ($Ag_5Sn$-beta phase is such an alloy). Moreover, the basic silver-tin (gamma) phase has the highest physical strength properties of all the major components of the standard or conventional ADA dental amalgam, including the silver-mercury and tin-mercury, gamma-1 and gamma-2, phases.

BRIEF DESCRIPTION OF THE INVENTION

This invention relates to dental amalgams having improved resistance to corrosion, tarnish and intergranular fracture. These desirable and beneficial results are achieved through the design of a two-component amalgam alloy system which, when the two components are combined and amalgamated with mercury, leads to the elimination of the corrodible tin-mercury (gamma-2) phase with a simultaneous reduction in the deleterious silver-mercury (gamma-1)phase.

The improved dental amalgam system of this invention has as a further object and purpose the maintenance of an increased amount of the silver-tin (gamma) phase constituent in the microstructure of the standard or conventional dental alloy, in order to secure the benefit of its singularly excellent resistance to tarnish and corrosion and its superior physical properties, in the resultant amalgam restoration. At the same time the amalgam of this invention is free of the undesirable and highly corrodible tin-mercury (gamma-2) phase.

Another object of the invention is to provide a second component alloy which readily amalgamates with mercury to provide the desired working quality or plasticity, and when combined and amalgamated with the cnventional first component silver-tin ($Ag_3Sn$) alloy acts as an effective "getter" for the corrodible tin in the tin-mercury (gamma-2) phase.

Yet another object of the invention is to provide a second component alloy for a dental amalgam having a sufficient oxidation resistance so that its exposure to ambient atmospheric conditions does not retard its amalgamation with the mercury.

Still a further object of the invention is the reduction in the amount of silver required for the amalgam, presently relatively expensive, whereby the dental amalgam of this invention has considerable economic importance and advantage.

DESCRIPTION OF PREFERRED EMBODIMENTS

A dental amalgam of this invention is fabricated by trituration of a combination of two metallic components in particulate form with mercury, wherein the mercury content comprises from about 40 to 60% by weight of the combined two components.

I

The first of the component alloys of this mixture comprises the standard or conventional dental amalgam alloy, formulated within the composition limits stated by the current American Dental Association Specification No. 1, which makes up 70 to 90% of the mixture. Such alloy component, identified as the first component alloy, comprises, by weight:

| | |
|---|---|
| Silver | 65.0% minimum |
| Tin | 29.0% maximum |
| Copper | 6.0% maximum |
| Zinc | 2.0% maximum |

According to European practice, mercury to 3.0% maximum may be added to the foregoing composition alloy. The remaining 10–30% of the mixture comprises one of the following copperbase alloys, as the second component alloy, preferably of but not necessarily limited to a particle size of 30 microns or less.

a. The second component alloy is one of the copper-silver alloys containing more than 50% copper. These alloys will meet and satisfy the objectives of the present invention. However, to maintain the silver-mercury phase in the amalgam to a low level, the second component alloys should preferably contain not more than 20.00% silver. Again, these alloys are subject to oxidation under ambient conditions and may hinder amalgamation. However, it has been found that if the particle size of these alloys is maintained below 15 microns, such oxidation as may be present will not adversely affect the dental amalgam and the purposes and advantages for which the alloy is designed.

b. Another second component alloy is one taken from the ternary and quaternary copper-base alloys containing silver, and/or tin, and/or zinc within the following composition limits (by weight):

| | |
|---|---|
| Copper | more than 50.00% |
| Silver | 0 – 49.00% |
| Tin | 0 – 10.00% |
| Zinc | 0 – 5.00% |

The above broad range of composition includes the following alloy systems:

b-1. Alloys comprising essentially copper-silver-tin in proportions of

| | |
|---|---|
| Silver | up to and including 49.00% maximum |
| Tin | up to and including 10.00% maximum |
| Copper | balance |

Preferred composition limits for these alloys are

| | |
|---|---|
| Silver | up to and including 20.00% maximum |
| Tin | up to and including 10.00% maximum |
| Copper | balance | and a preferred example of such an alloy comprises essentially

| | |
|---|---|
| Silver | 8.0% |
| Tin | 5.0% |
| Copper | Balance | b-2. Alloys comprising essentially copper-silver-zinc in proportions of

| | |
|---|---|
| Silver | up to and including 49% maximum |
| Zinc | up to and including 5% maximum |
| Copper | balance | and preferred composition limits for these alloys are

| | |
|---|---|
| Silver | up to and including 20.0% maximum |
| Zinc | up to and including 5.0% maximum |
| Copper | balance |

A preferred example of such an alloy comprises essentially

| | |
|---|---|
| Copper | 93% |
| Silver | 5% |
| Zinc | 2% | b-3. Alloys comprising essentially copper-tin-zinc in proportions of

| | |
|---|---|
| Zinc | up to and including 5% maximum |
| Tin | up to and including 10% maximum |
| Copper | balance |

A preferred range of composition for these alloys is

| | |
|---|---|
| Zinc | up to and including 5% maximum |
| Tin | up to and including 10% maximum |
| Copper | balance |

A preferred example of such an alloy is

| | |
|---|---|
| Copper | 93% |
| Tin | 5% |
| Zinc | 2% | b-4. Alloys containing copper-silver-tin-zinc in which the broad range of the elements is as follows:

| | |
|---|---|
| Copper | more than 50.0% |
| Silver | up to and including 49.0% maximum |
| Tin | up to and including 10.0% maximum |
| Zinc | up to and including 5.0% maximum |

A preferred range for this combination of elements is

| Silver | up to and including 20.0% maximum |
|---|---|
| Tin | up to and including 10.0% maximum |
| Zinc | up to and including 5.0% maximum |
| Copper | balance |

A preferred example of this quaternary alloy is

| Silver | 5% |
|---|---|
| Tin | 3% |
| Zinc | 2% |
| Copper | 90% |

The presence of silver, tin and zinc in the above alloy systems described in sections (b) through (b-4) above facilitate the amalgamation of the second component which is required for the handling characteristics or workability of the amalgam. Furthermore, these elements impart corrosion resistance to the second component alloy to improve the corrosion resistance of the amalgam, since the set amalgam will always contain some unreacted second component alloy. Again, in view of their greater solubility (than that of copper) in mercury, these elements counteract such limiting effects as may be due to oxidation of the second component alloy that hinders amalgamation.

c. An amalgamated second component alloy is one taken from the copper-base alloys containing silver, tin, zinc and mercury within the following broad range of composition:

| Copper | more than 50% |
|---|---|
| Silver | 0 – 49% |
| Tin | 0 – 10% |
| Zinc | 0 – 5%, and |
| Mercury | up to and including 20% maximum |

The above broad range of composition includes the following alloy systems:

c-1. Alloys of copper-mercury containing at least 80% copper. An example of such an alloy contains 90% copper and 10% mercury.

c-2. Alloys of copper-silver-mercury within the following broad composition limits:

| Silver | up to and including 49% maximum |
|---|---|
| Mercury | up to and including 20% maximum |
| Copper | balance |

Preferred composition limits for these alloys are

| Silver | up to and including 20% maximum |
|---|---|
| Mercury | up to and including 10% maximum |
| Copper | balance | and a preferred example is

| Copper | 90.0% |
|---|---|
| Silver | 5.0% |
| Mercury | 5.0% | c-3. Alloys of copper, tin and mercury in the following broad composition limits

| Tin | up to and including 10.0% maximum |
|---|---|
| Mercury | up to and including 20.0% maximum |
| Copper | balance |

Preferred composition limits for these alloys are

| Tin | up to and including 10.0% maximum |
|---|---|
| Mercury | up to and including 10.0% maximum |
| Copper | balance |

A preferred example:

| Copper | 90% |
|---|---|
| Tin | 5% |
| Mercury | 5% | c-4. Alloys of copper, zinc and mercury within the following broad composition limits

| Zinc | up to and including 5% maximum |
|---|---|
| Mercury | up to and including 20% maximum |
| Copper | balance |

Preferred composition limits for these alloys are

| Zinc | up to and including 5% maximum |
|---|---|
| Mercury | up to and including 10% maximum |
| Copper | balance |

A preferred example of such alloy is

| Copper | 93.0% |
|---|---|
| Zinc | 2.0% |
| Mercury | 5.0% | c-5. Alloys of copper, silver, tin and mercury within the broad composition limits -

| Silver | up to and including 49% maximum |
|---|---|
| Tin | up to and including 10% maximum |
| Mercury | up to and including 20% maximum |
| Copper | balance |

Preferred composition limits for these alloys are

| Silver | up to and including 20% maximum |
|---|---|
| Tin | up to and including 10% maximum |
| Mercury | up to and including 10% maximum |
| Copper | balance |

A preferred example of such alloy is

| Copper | 90.0% |
|---|---|
| Silver | 3.0% |
| Tin | 2.0% |
| Mercury | 5.0% | c-6. Alloys of copper, silver, zinc and mercury within the broad composition limits

| Silver | up to and including 49% maximum |
|---|---|
| Zinc | up to and including 5% maximum |
| Mercury | up to and including 20% maximum |
| Copper | balance |

Preferred composition limits for these alloys are

| Silver | up to and including 20% maximum |
|---|---|
| Zinc | up to and including 5% maximum |
| Mercury | up to and including 10% maximum |
| Copper | balance |

A preferred example of such alloy is

| Copper | 90.00% |
|---|---|
| Silver | 3.00% |
| Zinc | 2.00% |
| Mercury | 5.00% | c-7. Alloys of copper, tin, zinc and mercury within the broad composition limits

| Tin | up to and including 10% maximum |
|---|---|
| Zinc | up to and including 5% maximum |
| Mercury | up to and including 20% maximum |
| Copper | balance |

Preferred composition limits for such alloys are

| Tin | up to and including 10% maximum |
|---|---|
| Zinc | up to and including 5% maximum |
| Mercury | up to and including 10% maximum |
| Copper | balance |

A preferred example of such alloy is

| Copper | 90.0% |
|---|---|
| Tin | 3.0% |
| Zinc | 2.0% |
| Mercury | 5.0% | c-8. Alloys of copper, silver, tin, zinc and mercury within the broad composition limits

| Silver | up to and including 49% maximum |
|---|---|
| Tin | up to and including 10% maximum |
| Zinc | up to and including 5% maximum |
| Mercury | up to and including 20% maximum |
| Copper | balance |

Preferred composition limits of such alloys are

| Silver | up to and including 20% maximum |
|---|---|
| Tin | up to and including 10% maximum |
| Zinc | up to and including 5% maximum |
| Mercury | up to and including 10% maximum |
| Copper | balance |

A preferred example of such alloy is

| Copper | 90.0% |
|---|---|
| Silver | 3.0% |
| Tin | 1.0% |
| Zinc | 1.0% |
| Mercury | 5.0% |

Such preamalgamated alloys included in the systems described in (C) through (C-8) above, in addition to having the advantages and benefits of the unamalgamated second component alloys of the systems described in (b) through (b-4) above, offer the further advantage of ease and speed in amalgamation of the mixture with mercury.

An alloy formulated within the limits of the compositions described in (a), (b) through (b-4) and (c) through (c-8) above for the second component alloy, will satisfy the objectives and purposes for which the invention is designed. However, for the silver-containing second component alloys in (a), (b) through (b-4) and (c) through (c-8) above, the silver content is preferred on the low side rather than the high side of the range in order that the amount of the silvermercury (gamma-1) phase in the microstructure be held to a low level. The preferred silver content should not exceed 20.0% as has been indicated in the preferred ranges of compositions for those alloys which contain silver.

In the context of the disclosure in this application, the term "copper-base alloy" is to be understood to mean an alloy containing more than 50.0% copper by weight.

Both the first and second component alloys of the present invention may be supplied in the form of atomized powders, lathe-cut particles, filings, or tablets made therefrom.

Although particular embodiments of the invention have been disclosed herein for purposes of explanation, further modifications or variations thereof, after study of this specification, will or may become apparent to those skilled in the art to which the invention pertains. Reference should be had to the appended claims in determining the scope of the invention.

I claim:

1. An improved dental alloy consisting essentially of a mixture of a first component alloy and a second component alloy suitable for amalgamation with mercury to form an improved dental amalgam,
    a. said first component alloy consisting essentially of at least 65% silver, an operable amount of tin up to and including 29% maximum, an operable amount of copper up to and including 6% maximum, and an operable amount of zinc up to and including 2% maximum, by weight of said first component alloy;
    b. said second component alloy consisting essentially of a copper-silver alloy containing more than 50.00% copper;
    c. said first component alloy comprising about 70 to 90% by weight of said alloy mixture and said second component alloy comprising about 10 to 30% by weight of said alloy mixture.

2. The improved dental alloy defined in claim 1, and wherein said first component alloy further contains mercury up to and including 3% by weight of said first component alloy.

3. The new improved dental alloy defined in claim 1, wherein the silver content of said first component alloy is preferably in the range of from about 65% to and including 75% by weight of said first component alloy.

4. The new improved dental alloy defined in claim 1, wherein the tin content of said first component alloy is preferably in the range of from about 20% to and including 29% by weight of said first component alloy.

5. The new improved dental alloy defined in claim 2, wherein the silver content of said first component alloy is preferably in the range of from about 65% to and including 75% by weight of said first component alloy.

6. The new improved dental alloy defined in claim 2, wherein the tin content of said first component alloy is preferably in the range of from about 20% to and including 29% by weight of said first component alloy.

7. An improved dental alloy consisting essentially of a mixture of a first component alloy and a second component alloy suitable for amalgamation with mercury to form an improved dental amalgam,
    a. said first component alloy consisting essentially of at least 65% silver, an operable amount of tin up to and including 29% maximum, an operable amount of copper up to and including 6% maximum, and an operable amount of zinc up to and including 2% maximum, by weight of said first component alloy;
    b. said second component alloy consisting essentially of a ternary or quaternary copper-base alloy selected from the following metals within the following composition limits:

| Silver | up to and including 49.00%, |
|--------|------------------------------|
| Tin    | up to and including 10.00%, |
| Zinc   | up to and including 5.00%, |
| Copper | balance, | c. said first component alloy comprising about 70 to 90% by weight of said alloy mixture and said second component alloy comprising about 10 to 30% by weight of said alloy mixture.

8. The new improved dental alloy defined in claim 7, wherein said first component alloy further contains mercury up to and including 3% by weight of said first component alloy.

9. The new improved dental alloy defined in claim 7, wherein the silver content of said first component alloy is preferably in the range of from about 65% to and including 75% by weight of said first component alloy.

10. The new improved dental alloy defined in claim 7, wherein the tin content of said first component alloy is preferably in the range of from about 20% to and including 29% by weight of said first component alloy.

11. The new improved dental alloy defined in claim 8, wherein the silver content of said first component alloy is preferably in the range of from about 65% to and including 75% by weight of said first component alloy.

12. The new improved dental alloy defined in claim 8, wherein the tin content of said first component alloy is preferably in the range of from about 20% to and including 29% by weight of said first component alloy.

13. An improved dental alloy consisting essentially of a mixture of a first component alloy and a second component alloy suitable for amalgamation with mercury to form an improved dental amalgam,
 a. said first component alloy consisting essentially of at least 65% silver, an operable amount of tin up to and including 29% maximum, an operable amount of copper up to and including 6% maximum, and an operable amount of zinc up to and including 2% maximum, by weight of said first component alloy;
 b. said second component alloy consisting essentially of a binary, ternary, quaternary or quinary amalgamated copperbase alloy selected from the following metals within the following composition limits:

|     | Silver  | up to and including 49.00% |
|-----|---------|----------------------------|
|     | Tin     | up to and including 1.00% |
|     | Zinc    | up to and including 5.00% |
|     | Mercury | up to and including 20.00% maximum |
| and | Copper  | balance, | c. said first component alloy comprising about 70 to 90% by weight of said alloy mixture and said second component alloy comprising about 10 to 30% by weight of said alloy mixture.

14. The new improved dental alloy defined in claim 13, wherein said first component alloy further contains mercury up to and including 3% by weight of said first component alloy.

15. The new improved dental alloy defined in claim 13 wherein the silver content of said first component alloy is preferably in the range of from about 65% to and including 75% by weight of said first component alloy.

16. The new improved dental alloy defined in claim 13, wherein the tin content of said first component alloy is preferably in the range of from about 20% to and including 29% by weight of said first component alloy.

17. The new improved dental alloy defined in claim 14, wherein the silver content of said first component alloy is preferably in the range of from about 65% to and including 75% by weight of said first component alloy.

18. The new improved dental alloy defined in claim 14, wherein the tin content of said first component alloy is preferably in the range of from about 20% to and including 29% by weight of said first component alloy.

* * * * *

UNITED STATES PATENT OFFICE
CERTIFICATE OF CORRECTION

Patent No. 3,963,484   Dated   June 15, 1976

Inventor(s)  Nikhil K. Sarkar

It is certified that error appears in the above-identified patent and that said Letters Patent are hereby corrected as shown below:

Column 10, line 10, "the percentage of Tin" to read:
--- Tin    up to and including 10.00% ---.

Signed and Sealed this

Tenth Day of October 1978

[SEAL]

Attest:

RUTH C. MASON
Attesting Officer

DONALD W. BANNER
Commissioner of Patents and Trademarks